United States Patent [19]

Kung et al.

[11] 4,051,164

[45] Sept. 27, 1977

[54] ENOL ESTER OF α-DIKETONES

[75] Inventors: Jo-Fen Tung Kung, North Bergen, N.J.; Martin Franklin Epstein, Pearl River, N.Y.

[73] Assignee: General Foods Corporation, White Plains, N.Y.

[21] Appl. No.: 647,952

[22] Filed: Jan. 9, 1976

Related U.S. Application Data

[62] Division of Ser. No. 550,102, Feb. 14, 1975, abandoned, which is a division of Ser. No. 453,222, March 21, 1974, abandoned.

[51] Int. Cl.$^2$ .............................................. C07F 7/18
[52] U.S. Cl. ........................................ 260/448.8 R
[58] Field of Search ................................. 260/448.8 R

[56] References Cited

U.S. PATENT DOCUMENTS

| 3,472,888 | 10/1969 | Bazouin et al. ............... 260/448.8 R |
| 3,985,813 | 10/1976 | Labovitz et al. ......... 260/448.8 R X |

Primary Examiner—Paul F. Shaver
Attorney, Agent, or Firm—Daniel J. Donovan; Bruno P. Struzzi; Doris M. Bennett

[57] ABSTRACT

Flavoring agents, a method of imparting to foodstuffs a pleasant buttery caramel flavor and aroma by adding thereto a lower alkyl enol ester such as an acetate ester of aliphatic and alicyclic α-diketones.

2 Claims, No Drawings

ENOL ESTER OF α-DIKETONES

This is a division of application Ser. No. 550,102, filed 2-14-75, now abondoned, which is a division of application Ser. No. 453,222, filed Mar. 21, 1974, now abondoned.

BACKGROUND OF THE INVENTION

The present invention relates to new flavoring agents capable of imparting to foodstuffs the taste of buttery caramel. More specifically, the invention relates to lower alkyl enol esters of aliphatic and alicyclic α-diketones and their use as flavoring and aromatizing agents.

SUMMARY OF THE INVENTION

It has now been found that alicyclic and aliphatic α-diketones such as 2,3-pentanedione can be enolized under specific conditions. The resulting enol forms have a buttery caramel flavor and aroma but due to their instability are limited as to their use as flavoring agents. However, when these compounds are stabilized by silylation or acetylation, stable flavoring and aromatizing agents are derived.

The pleasant, buttery caramel flavor and aroma of these compounds was first discovered when the enol form of 2,3-pentanedione i.e. 3-hydroxy-3-penten-2-one was isolated from a coffee aroma concentrate. When converted to its stable trimethyl silyl ether or acetate ester, 3- penten -2-one, 3-hydroxy acetate, two new compounds which demonstrate the desirable buttery caramel flavor and aroma of the unmodified enol are derived. The acetate esters are preferred where the compounds of this invention are to be employed in foodstuffs. Therefore, reference will henceforth be made principally to the use of the acetate esters when speaking in terms of incorporating the compounds of this invention into foodstuffs.

Due to the fact that the acetate esters of these alicyclic and aliphatic α-diketones are stable as pure liquids or in non-polar solutions, the flavoring agents of this invention find application as flavoring agents incorporated into liquid or non-polar solvent carriers for use in dry, and liquid foodstuffs in which a natural buttery caramel or butterscotch flavor is desired. The amount to be added depends both on the system and the degree of flavor and aroma desired.

DESCRIPTION OF THE INVENTION

The acetate esters of this invention are 1-buten-3-one, 2-hydroxyacetate; 3-hexen-4-one, 3-hydroxy acetate; 3-penten-2-one, 3-hydroxy acetate; cyclohex-1-en-2-one, 1-hydroxy acetate, 3-hexen-4-one, 3-hydroxy butyrate; 3-penten-2-one, 3hydroxy butyrate; cyclohex-1-en-2-one, 1-hydroxy butrate; 3-hexen-4-one, 3-hydroxy propionate; 3-penten-2-one, 3-hydroxy propionate; cyclohex-1-en-2-one, 1-hydroxy propionate and the like. In the interest of succinctness and clarity, reference will henceforth be made principally to the preparation and use of 3-penten-2-one, 3-hydroxy acetate a new compound, but it is not wished to restrict this invention to the same.

Generally, the enol form of an aliphatic or alicyclic α-diketone devoid of $CH_2$ groups may be prepared by three methods. The α-diketone preferably having been re-distilled, may be injected directly into a gas chromatograph having an injection port temperature of at least about 300° C, the higher temperature helping actually to form the enol. Although this method is the most direct in terms of obtaining the pure enol, the amount of enol derived is necessarily small due to injection of the pure α-diketone and such method may not therefore be preferred where large amounts of the enol are desired. Secondly, the α-diketone may be enolized at lower temperatures by combining the same with an acid such as hydrochloric acid or sulfuric acid, heating the mixture to about 100° C to 125° C and extracting the enol from the cooled mixture by means of a non-polar solvent. The pure enol may subsequently be isolated from the extract by distillation or gas chromatography. The injection port temperature need not be as high as 300° C in this instance since the enol is already formed and therefore conventional methods of gas chromatography may be employed. The third method is the direct obtention of the enol ester of the α-diketone by the acid catalyzed reaction of the α-diketone and an acetylating agent. Some of the acids which may be employed are for example, trifluoroacetic acid, methyl sulfonic acid, p-toluenesulfonic acid, boron trifluoride etherate and the like. Similarly, exemplary of the acetylating agents are isopropenyl acetate and acetic anhydride. This method is preferred over the previously mentioned methods since it affords a means of deriving the acetate esters of the present invention by the concurrent enolization and acetylation of the α-diketones. As mentioned previously the enols of this invention are unstable and therefore require subsequent or concurrent conversion to their stable acetate ester or trimethyl silyl ether forms, the acetate ester being preferred where the stabilized enol is to be employed in a food or beverage system.

A detailed explanation of the preparation of the enol form of α-diketones, and the subsequent stabilization of the same to the silyl ether and acetate ester follows. Although methods of purification are also discussed, purification of the reaction product is not necessary in order that the buttery notes of these compounds be demonstrated. However, where the acetate esters are to be incorporated into foodstuffs, purification is preferred. It should be apparent to those skilled in the art that obvious variations in both the concentrations of the reactant materials and the operating conditions employed in the methods of preparing the silyl ether and acetate ester from the enol may be made without appreciably affecting the final product or the inherent qualities of the same.

EXAMPLE I 100 mg portions of redistilled 2,3-pentanedione are injected into a Perkin-Elmer Model 800 gas chromatograph with a flame-ionization detector and effluent splatter, and dual stainless steel columns (⅛inch × 6feet) packed with 15% OV-101 on Anakrom ABS, 80/90 mesh size.

The operating conditions are as follows:
a. Injection port temperature is maintained at 300° C to 350° C;
b. the column temperature is 4 minutes at 70° C, then programmed to 300° C at 5° minute;
c. the detector temperature is 300° C;
d. helium flow rate, 30 ml/minute;
e. hydrogen, 30 psi;
f. air flow rate, 360 ml/minute.
g. The component elutes at 3.5 minutes and contains mainly enol form and has a caramel-buttery aroma. It is collected into a melting point tube cooled with dry ice. The collected material is dissolved in a small amount of Freon 113 and the enol form is purified by rechromatography of the Freon solution on a Perkin-Elmer Model 900 gas chromatograph, with a flame ionization detector and effluent splitter, and dual stainless steel columns (⅛inch × 6feet) packed with 15% stabilized DEGS on Anakrom ABS, 80/90 mesh size. The operating conditions of the second purification process are as follows: Injection port temperature, 180° C; column temperature, 50° to 175° C at 2.5° minute; detector temperature, 180° C; helium flow rate, 17 ml/minute; hydrogen, 22 psi; air flow rate, 54 psi. The injection port temperature is kept at 175°–180° C in order to prevent thermal degradation of the enol form at higher temperatures. The pure enol ($R_t$ of 12.9 minutes) is trapped into a melting point tube as described above. The un-enolized 2,3-pentanedione elutes at 5.8 minutes.

EXAMPLE II 2,3-Pentanedione is enolized to 3-hydroxy-3-penten-2-one by mixing with hydrochloric acid in a ratio of 2:1 by weight of the α-diacetone to HCL in a closed container. The mixture is heated at about 110° C for about an hour. After being cooled to room temperature, the mixture is extracted with Freon 113. The enol form in the extract is then isolated by GC having an injection port temperature maintained at between about 300° C and 350° C.

EXAMPLE III

3-Penten-2-one, 3-hydroxy acetate is prepared by combining 2,3-pentanedione with acetic anhydride and p-toluenesulfonic acid, the amount of anhydride being about 1½ to 4 times the concentration of acid on a molar basis. The mixture is cooled for about ½ hour. The reaction mixture is allowed to stand at room temperature after the initial cooling for a moderately long period, usually about 16 hours. The mixture is thereupon cooled for a second time and water is added. The cooling source is removed after about one hour and after about 3 hours, the reaction mixture is diluted with ether. The ether layer is washed with water, 5% sodium bicarbonate and water. The ether extract is dried over sodium sulfate and is then concentrated and distilled. The product is subsequently purified by gas chromatography on a 15% SP-2100 column ⅛inch × 12, feet, programmed between 80° C and 175° C.

EXAMPLE IV

The pure 3-hydroxy-3-penten-2-one of Example II is converted to its stable silyl ether form with hexamethyldisilazane and trimethylchlorosilane immediately after GC isolation. The silyl ether is then separated from the excess reagents by chromatographing on the P-E 900 with 15% DEGS column. It has a retention time of 10.7 minutes under the conditions previously described.

What is claimed is:
1. The silyl ether of the enol of pentane-2,3-dione which imparts to foodstuffs a buttery, caramel flavor.
2. The trimethylsilyl ether of the enol of pentane-2,3-dione.

* * * * *